United States Patent [19]
Amidon et al.

[11] Patent Number: 6,153,592
[45] Date of Patent: *Nov. 28, 2000

[54] ENHANCING THE BIOAVAILABILITY OF PROTEOLYTICALLY LABILE THERAPEUTIC AGENTS

[75] Inventors: Gordon L. Amidon, Ann Arbor, Mich.; Glen D. Leesman, Hamilton, Mont.; Patrick J. Sinko, Lebanon, N.J.

[73] Assignee: Port Systems, LLC, Ann Arbor, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/244,715
[22] PCT Filed: Nov. 9, 1992
[86] PCT No.: PCT/US92/09336
  § 371 Date: Sep. 8, 1994
  § 102(e) Date: Sep. 8, 1994
[51] Int. Cl.$^7$ .......................... A61K 38/23; A61K 38/16
[52] U.S. Cl. .............................. 514/21; 514/12; 530/397; 530/399
[58] Field of Search ................. 514/21, 12; 530/399, 530/397

[56] References Cited

U.S. PATENT DOCUMENTS

| | | | |
|---|---|---|---|
| 4,131,607 | 12/1978 | Petit et al. | 260/5 |
| 4,579,730 | 4/1986 | Kidron et al. | 424/19 |
| 4,639,435 | 1/1987 | Fujii et al. | 514/11 |
| 4,774,089 | 9/1988 | Ashmead | 424/157 |
| 5,206,219 | 4/1993 | Desai | 514/3 |

FOREIGN PATENT DOCUMENTS

| | | |
|---|---|---|
| 0090886 | 10/1983 | European Pat. Off. . |
| 0127535 | 12/1984 | European Pat. Off. . |
| 0266950 | 5/1988 | European Pat. Off. . |
| 0371195 | 7/1988 | European Pat. Off. . |
| 0327756 | 8/1989 | European Pat. Off. . |
| 0341661 | 11/1989 | European Pat. Off. . |
| 252539 | 12/1987 | Germany . |
| 9003164 | 4/1990 | WIPO . |

OTHER PUBLICATIONS

Parsons et al., Br. J. Pharmocol., vol. 66, pp. 25–32, 1979.
Doron I Friedman and Gordon L. Amidon, "Oral Absorption of Peptides: Influence of pH and Inhibitors on the Intestinal Hydrolysis of Leu–Enkephalin and Analogues", Pharamaceutical Research, vol. 8, No. 1, 93–96, (1991).
Jabar A. Faraj, et al., "Mechanism of Nasal Absorption of Drugs.III: Nasal Absorption of Leucine Enkephalin", Journal of Pharmaceutical Sciences, vol. 79, No. 8, 698–702, (1990).
Vincent H. L. Lee, "Protease Inhibitors and Penetration Enhancers as Approaches to Modify Peptide Absorption", Journal of Controlled Release, 13, 213–223, (1990).
E. Ziv,O. Lior and M. Kidron, "Absorption of Protein Via the Intestinal Wall—A Quantitative Model", Biochemical Pharmacology, vol. 36, No. 7, 1035–1039, (1987).
Anwar Hussain, et al., "Hydrolysis of Leucine Enkephalin in the Nasal Cavity of the Rat—A Possible Factor in the low Bioavailability of Nasally Administered Peptides", Biochemical and Biophysical Research Communications, vol. 133, No. 3, 923–928, (1985).
Ryohei Hori, Fusao Komada and Katsuhiko Okumura, "Pharmaceutical Approach to Subcutaneous Dosage Forms of Insulin", Journal of Pharmaceutical Sciences, vol. 72, No. 4, 435–439, (1983).
Allan K. Smith, Sidney J. Circle and George H. Brother, "Peptization of Soybean Proteins. The Effect of Neutral Salts on the Quality of Nitrogenous Constituents Extracted from Oil–Free Meal", Journal of the American Chemical Society, vol. 60, 1316–1320, (1938).
Rompp Chemie Lexikon, 9th ed., 1989, pp. 232 and 733.
Rompp Chemie Lexikon, 8th ed., 1979, pp. 4382–4383.

*Primary Examiner*—Chhaya D. Sayala
*Attorney, Agent, or Firm*—Gifford, Krass, Groh, Sprinkle, Anderson & Citkowski, P.C.

[57] ABSTRACT

Proteins or peptidic substances, which may be prepared from naturally occurring proteins, enhance the bioavailability of proteolytically-labile therapeutic agents which, in the absence of the protein or peptidic substance would suffer enzymatic inactivation upon administration.

17 Claims, No Drawings

ENHANCING THE BIOAVAILABILITY OF PROTEOLYTICALLY LABILE THERAPEUTIC AGENTS

This invention relates to enhancing the bioavailability of proteolytically labile therapeutic agents by administering the therapeutic agent in combination with a protecting agent comprising a protein, a purified natural protein, a molecular weight fractionated protein, or a partially hydrolyzed protein.

BACKGROUND OF THE INVENTION

Peptide drugs and drugs containing a peptidase labile bond are among the most promising medicinal agents of modern times, but their instability in the presence of proteolytic enzymes in the gastrointestinal tract and other mucosal tissues usually requires that they be administered parenterally. Although patients can be taught to inject parenterally, there has been a long felt need to develop a non-invasive method for self administration of peptide drugs.

Protease inhibitors and penetration enhancers are means often considered to circumvent the enzymatic and penetration barriers to peptide and protein absorption from mucosal routes of administration. Because of such barriers, the bioavailability of peptide and protein drugs from mucosal routes is poor.

Non-parenteral administration of peptide drugs in particular often results in very low bioavailability because of hydrolysis of the peptides by proteolytic enzymes. For leuprolide, this ranges from 0.05% following oral administration to 38% following vaginal administration; for insulin, the corresponding figures are 0.05% and 18%. Lee, Journal of Controlled Release, 13, 213 (1990).

Examples of proteolytic enzymes which inactivate proteolytically-labile therapeutic agents are pepsin, trypsin, chymotrypsin, elastase, and carboxypeptidase in the intestinal lumen, and the aminopeptidases located on the mucosal surfaces of the GI tract, nose, and vagina.

Transport of intact oligopeptides across adult mammalian jejunum has been demonstrated in vitro and in vivo as well as in combination with peptidase inhibitors. Friedman and Amidon, *Pharmaceutical Research* 8, no. 1, P. 93, (1991).

Fujii et al; U.S. Pat. No. 4,639,435 (1987) claims the use of 1-isopropyl-4-[4-(1,2,3,4-tetrahydronaphthoyloxy) benzoyl] piperazine methanesulfonate as an inhibitor of chymotrypsin to be co-dosed orally or rectally with a chymotrypsin-labile drug (kallikrein or calcitonin). The reference also discloses the use of benzoylpiperazine esters for this purpose. The reference does not describe the mechanism of these inhibitors.

Cho and Flynn; International Patent Application WO-90/03164 (1990) disclose the use of protease inhibitors in oral formulation but do not describe the nature of such inhibitors in detail; the only protease inhibitor which appears in the examples is aprotinin.

Kidron, et al; U.S. Pat. No. 4,579,730 (1986) disclose the use of protease inhibitors in oral formulation of insulin. Soybean flour is disclosed as a source of soybean trypsin inhibitor (Bowman-Birk trypsin/chymotrypsin inhibitor; molecular weight 8000 daltons).

Ziv, et al; Biochem. Pharmacol. 36, 1035–1039 (1987) disclose the use of the protease inhibitor aprotinin to enhance the oral absorption of proteins.

Losse, et al; East German Patent DD 252 539 A1 (1987) disclose the use of epsilon-aminocaproic acid and aprotinin as protease inhibitors in oral formulation of peptides.

Lee; J.; Controlled Release 13, 213–223 (1990) reviews the use of protease inhibitors in formulations of peptides for oral, nasal, buccal, rectal, vaginal, pulmonary, and ocular routes.

Certain small peptides containing up to four amino acids have been shown to enhance the bioavailability of peptide drugs.

Hussain, et al, Biochemical and Biophysical Research Communications, 133, no. 3, 923 (195) suggested that nasal administration of peptides may become an important route provided that peptidases in the nasal mucosa can be transiently inhibited via coadministration of pharmacologically inactive peptidase substrates.

Faraj, et al, Journal of Pharmaceutical Sciences 79, no. 8, 698 (1990) showed that in the presence of the small peptides, L-tyrosyl-L-tyrosine and tri-L-tyrosine methyl ester, the hydrolysis of leucine enkaphalin was reduced, suggesting that competitive inhibition of nasal peptidases was caused by these small peptides.

Hori et al; J. Pharm. Sci. 72, 435–439 (1983), disclose the use of various amino-protected peptides to protect insulin from degradation when injected subcutaneously. Numerous publications disclose enzymatic treatment of vegetable proteins. An early U.S. Patent No. by John R. Turner (U.S. Pat. No. 2,489,208) discloses a pepsin modified whipping agent component. An alkaline material such as sodium sulfite, sodium carbonate or sodium hydroxide is used to extract glycinin at a pH 6.4–6.8. The glycinin is then precipitated from the extract (e.g., pH 4.2–4.6) at its isoelectric pH in which sulfur dioxide may be utilized as the adjusting acid. The precipitated glycinin product is then modified with pepsin under temperature and pH conditions conducive to hydrolysis of protein. The glycinin is hydrolyzed with pepsin until its water-solubility is increased to 40–50%. Similarly, U.S. Pat. No. 2,502,482 by Sair et al. reports the enzymatic modification of glycinin with pepsin to produce an isolate wherein at least 60% by weight of the pepsin modified isolate is water-soluble at a pH 5.0.

Puski reports the enzymatic modifying of soy isolates (precipitated at pH 4.5) with *Aspergillus oryzae* in "Modification of Functional Properties of Soy Proteins by Proteolytic Enzyme Treatment" (Cereal Chem. 52, pages 655–665 (1975)).

Several publications also report using saline solutions to extract soy proteins. A publication by A. K. Smith et al. (Jr. American Chemical Society, Vol. 60, June 1938, pages 1316–1320) reports the extraction of soybean meal with pH 6.7 water alone yields more protein extract than an aqueous extraction in the presence of neutral salts.

U.S. Pat. No. 4,131,607 by Petit discloses a two-stage alkaline extraction. The extraction is initially conducted in the presence of sodium sulphite and magnesium salt at a pH 7.0–8.5 which is then increased to a pH 10.0–10.5 to complete the extraction. The protein extras are then precipitated or curded by adjusting the extract to a pH 4.5–5.5. A patent issued to Martinez et al. (U.S. Pat. No. 3,579,496) similarly discloses a multiple solvent extraction process.

SUMMARY OF THE INVENTION

We have found that proteins, peptides, purified natural proteins, and filtered, solvent-extracted, molecular weight-fractionated or partially hydrolyzed proteins hereinafter referred to as protecting agents enhance the oral, nasal, rectal and vaginal bioavailability of proteolytically-labile therapeutic agents which, in the absence of the protecting agents, would suffer enzymatic inactivation upon attempted oral, nasal, rectal or vaginal administration.

DETAILED DESCRIPTION OF THE INVENTION

This invention comprises a protecting agent and a pharmaceutically effective amount of a proteolytically-labile therapeutic agent, with the proviso that when said protecting agent is soy flour said therapeutic agent may not be insulin.

In another aspect this invention comprises a method of enhancing bioavailability of a proteolytically-labile therapeutic agent to a mammal or other animal in need of said therapeutic agent comprising administering said therapeutic agent in combination with a bioavailability enhancing amount of protecting agent with the proviso that when said protecting agent is soy flour said therapeutic agent may not be insulin.

A proteolytically-labile therapeutic agent, which is an active ingredient in a pharmaceutical composition of the invention, includes those which possess peptide bonds in their structure or which, upon exposure to various proteolytic enzymes present in the digestive tract or nasal or vaginal mucosa, are inactivated by decomposition, denaturation or other means. When administered orally, nasally, rectally or vaginally, therefore, the active therapeutic agents cannot be absorbed or cannot produce their therapeutic effects to a satisfactory extent.

Examples of such proteolytically-labile therapeutic agents are peptides, such as calcitonin, prolactin, adrenocorticotropin, thyrotropin, growth hormone, gonadotropic hormone, oxytocin, vasopressin, gastrin, tetragastrin, pentagastrin, glucagon, secretin, pancreozymin, substance P and gonadotropin. Other examples of proteolytically-labile therapeutic agents are luteinizing releasing hormone, leuprolide, enkephalin, follicle stimulating hormone, cholecystokinin, thymopentin, endothelin, neurotensin, interferon, interleukins, insulin, and insulinotropin. Other examples are therapeutic antibodies, such as those used to treat septic shock.

As the proteolytically-labile therapeutic agents, there may also be used purified extracts of natural origin and their chemical modifications as well as products obtained by tissue culture and products obtained by cultivating microorganisms or cells rendered productive by genetic engineering techniques. The proteolytically-labile therapeutic agents may also include synthetic peptides and derivatized synthetic peptides such as Terlakiren (U.S. Pat. No. 4,814,342).

Protecting agents of the present invention may be chemically synthesized proteins and peptides, natural proteins, purified natural proteins, chemically modified natural proteins or partially hydrolyzed natural proteins, or proteins which have been fractionated according to molecular weight, polarity, or charge, or mixtures thereof. Natural, food-grade proteins or partially hydrolyzed food-grade proteins are preferred. The molecular weight of the protecting agent should be greater than 1000.

The procedures for molecular weight fractionation of the protecting agent may be varied to produce any desired molecular weight fraction of a natural protein. Solvent extraction may be used to separate proteins according to molecular weight, polarity or charge. Enzymatic or chemical hydrolysis of a protein may be followed by separation of the desired molecular weight fraction by ultrafiltration membranes or dialysis membranes. Molecular weight fractionation may also be effected by gel chromatography or other means.

Hydrolysis of proteins or peptides may be carried out by heat treatment, or by treatment with acid or base or cyanogen bromide or by other chemical means.

Enzymatic treatment may be carried out with a single proteolytic enzyme, or with various combinations of proteolytic enzymes, acting concurrently or sequentially. A variety of proteolytic enzymes may be used, including but not limited to trypsin, chymotrypsin, elastase, carboxypeptidase, aminopeptidase, pepsin, and collagenase.

Fractionation and enzymatic treatments to produce the protecting agents of this invention may be applied to a wide variety of proteinaceous materials. Naturally occurring proteins of animal or vegetable origin are preferred. Such proteinaceous starting materials include but are not limited to soy flour, soy protein, wheat gluten, almond powder, peanut powder, casein, fish protein, and the like.

Without intending to be limited thereby, it is believed that the protecting agents of this invention function as sacrificial protease inhibitors which thereby enhance the bioavailability of pharmaceutical agents that are labile to certain proteases that can degrade the pharmaceutical agents upon oral, nasal, vaginal or rectal administration. Coadministration of these protecting agents with the labile pharmaceutical agents results in (1) competitive occupancy of the degrading proteases by said protecting agents, (2) inhibition of protease degradation of the pharmaceutical agents resulting in enhanced absorption and therapeutic effectiveness, and (3) ultimate metabolism and absorption of the protecting agents.

In view of the above-proposed mechanism of action it is believed to be desirable to match the dissolution rate of the protecting agent to the dissolution rate of the proteolytically-labile therapeutic agent. Generally, we have found that short dissolution times of the protecting agent are more effective for low molecular weight therapeutic agents. Peptides ranging in molecular weight of >1000 to <100,000 are preferred, with a molecular weight of >1000 to <30,000 being especially preferred.

The effective protecting agent fraction must be matched to the particular lability characteristics of the proteolytically-labile therapeutic agent. Thus, for a therapeutic agent which possesses aminopeptidase lability, a protecting agent fraction which has a fast dissolution rate and is effective against aminopeptidase is preferred. For the aminopeptidase-labide therapeutic agent D-Ala-D-Leu-enkephalin (YdAGFdL), a preferred protecting agent is the <30,000 MW fraction of pepsin-treated decanted soy flour, as demonstrated in Example 15. In general, for a proteolytically-labile therapeutic agent possessing lability to one or more lumenal or mucosal proteases, a preferred protecting agent is one which improves the systemic bioavailability of the therapeutic agent when the protecting agent is dosed at a practical total dose, as described above. Preferred protecting agent fractions, for a particular proteolytically-labile therapeutic agent, are obtained by the decanting, filtration, extraction, hydrolysis, and size fractionation processes described herein. Preferred protecting agent fractions for a particular proteolytically-labile therapeutic agent are identified utilizing in vitro and in vivo procedures such as those exemplified herein.

The pharmaceutical composition according to the present invention is preferably administered to a mammal or other animal in need of such treatment in any form in which a protecting agent and proteolytically-labile therapeutic agent are allowed to coexist in the intestine, for example, in the form of tablets, granules or capsules, with both ingredients provided with an enteric coating either separately or compositely. The composition may also be administered rectally or vaginally in the form of suppositories prepared by adding both ingredients to a suppository base in ordinary use.

Likewise, the protecting agent and proteolytically-labile therapeutic agent may be dosed together in a nasal spray. Where desirable, these dosage forms may be added with various pharmaceutically acceptable additives such as excipients and emulsifiers.

The dose of the proteolytically labile therapeutic agent is preferably 0.0001 to 1 times the dose if such substance is administered orally in the prior art. The amount of the protecting agent will depend upon the route of administration, the lability of the therapeutic agent, and the dose of the therapeutic agent. For oral, rectal, and vaginal administration, the protecting agent will generally be dosed at about 10-1500 mg. In the case of orally-dosed solutions or suspensions, the protecting agent will be dosed at 10 mg to about 15 gm. For nasal administration, the dose of protecting agent will be generally lower, in the range about 1–100 mg.

Several pharmaceutical compositions for intestinal absorption according to this invention were evaluated with respect to their effectiveness, with the results given below.

The following examples are intended only to further illustrate the invention and are not intended to limit the scope of the invention which is defined by the claims.

EXAMPLE 1

Processing of Commercial Proteins and Flours. Fractionation by Solubilization. Soy Flour.

Soy Flour (from Sigma Chem. Co.), 4.5 g in 135 ml 0.01M pH 7.5 phosphate buffer and 15 ml 0.05% Thimerosal was stirred for 15 minutes, sonicated for 10 minutes and agitated for 25 hours at room temperature. The mixture was allowed to settle, the supernatant drawn off, centrifuged, and filtered. In this way the directly-soluble fraction was obtained for recovery and use or further processing.

EXAMPLE 2

Processing Of Commercial Proteins and Flours. Molecular Weight Fractionation by Solubilization and Dialysis. Soy Flour The procedure of Example 1 was followed to prepare a solution of decanted and filtered soy flour which was processed further as follows to achieve molecular weight (MW) discrimination. The solubilized fraction was evaporated to dryness at 55° C. in a vacuum oven. The evaporate was dissolved in water and dialyzed in 1000 Molecular Weight Cut-Off (MWCO) Spectrum dialysis tubing against water over a period of 24 hours with periodic changes of dialysing medium. The retentates were evaporated giving 1.17 g of a >1000 MW solubilized soy flour fraction.

EXAMPLE 3

Processing of Commercial Proteins and Flours. Molecular Weight Fractionation by Solubilization and Ultrafiltration (UF): 1K–30K and 30K–100K Fraction.

Commercial Soy Flour, Sigma No. S-9633 (288 g) was added with stirring to a solution of 8640 ml of an 0.01M pH 7.5 phosphate buffer and 1920 ml of 0.1% Thimerosal. The suspension was mixed for an additional 15 minutes with a magnetic stirrer. The mixture was then sonicated for 10 minutes and then stirred at room temperature for 24 hours. The solution was then centrifuged at 2500–3000 rpm for 1 hour. The supernatant liquid was separated by ultrafiltration using a 100K Nominal Molecular Weight Unit Pellicon (Millipore Corp., Bedford, Mass.) Membrane. The retentate (>100K) was discarded, and the permeate (<100K) was separated using a 30K nominal molecular weight Pellicon membrane. The second (30K–100K) was saved, and the second permeate was separated on a 1K nominal molecular weight Pellicon membrane. The third retentate (1K–30K was saved, and the third permeate (<1K) was discarded. The 1K–30K fraction was freeze-dried, and the 30K–100K fraction was dried in a vacuum oven. The yield of the 1K–30K fraction (7.33 g) was 2.5% of the starting soy flour. The yield of the 30K-100K fraction (5.25 g) was 1.8% of the starting soy flour.

EXAMPLE 4

Processing of Commercial Proteins and Flours. Hydrolysis by Pepsin and Molecular Weight Fractionation by Dialysis. Soy Flour Soy flour was hydrolysed into lower molecular weight (MW) fragments using pepsin and the hydrolysate was fractionated into 1000–3500, 3500–6/8K and 6/8K–12/14K MW fractions according to the following procedure.

Soy flour (Sigma # S-99633; 5.4 g) and Thimerosal (50 ppm in final concentration) were added to 180 ml of a solution containing pH 1.9 0.2N KCl/0.2 N HCl and mixed for one-half hour after which Pepsin (Sigma #P-6887; 18.0 mg) was added. Aliquots of 20 ml each were placed in each of 9 pieces of 12,000–14,000 Molecular Weight Cut-Off (MWCO) Spectrum dialysis tubing, and were dialyzed against 55 ml of pH 1.9 KCl buffer at 37° C. in a shaking water bath. The buffer was changed after 2 hours and after 6 hours and dialysis was continued for 24 hours. Permeates (<12/14K) from each time period were combined and evaporated at 55° C. in a vacuum oven.

The 2, 6 and 24 hour samples were placed in 1000 MWCO tubing and dialyzed against water. The resulting retentates (1K–12/14K) were evaporated at 55° C. in a vacuum oven, giving a total weight of 449.5 mg; 418 mg of this material was dissolved in 30 ml deionized water and placed in two pieces of 3500 MWCO dialysis tubing, and dialyzed against 55 ml water at room temperature for 24 hours. The water was changed after 2, 6 and 24 hours dialysis, and the permeates (1K–3.5K) were combined and evaporated at 55° C. in a vacuum oven.

The retentates from each piece of tubing were each placed in 6000/8000 MWCO tubing and treated as above. Evaporation of the permeates provided fragments of 3500–6000/8000 MW. The retentates, representing the 6000/8000–12000/14000 MW fraction, were also combined and evaporated. Scheme I summarizes the described fractionation procedure.

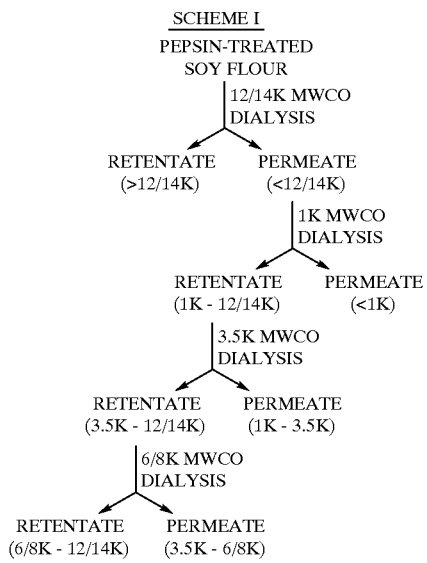

SCHEME I
PEPSIN-TREATED SOY FLOUR

EXAMPLE 5

Processing of Proteins and Flours. Treatment with immobilized Pepsin.

Soy flour (Sigma Chem. Co.; S-9633) was processed as in Example 1, and was dried. This material was ultrafiltered with a 30K MWCO membrane. The retentate (<30K) was collected and dried. 13.8 g of this material was dissolved in 900 ml water, and the pH was adjusted to pH 2.0 with 0.1 N HCl. 1.19 g immobilized pepsin (immobilied on 4% cross-linked beaded agarose Sigma Chemical Co.; P-3286; 40 units/mg) was added. This suspension, maintained at 37° C., was ultrafiltered through three 30K MWCO membranes. The permeate (<30K) was collected in 15 minute intervals and was freeze-dried. The retentate (>30K) was recycled through ultrafiltration processing. The products of pepsin hydrolysis appear in the permeate. Table I presents the volume of each permeate fraction, and the mass of hydrolyzed peptide in each dried fraction.

TABLE I

Yield of pepsin hydrolyzed peptides, obtained through the methods described in Example 5.

| Collection Time (min) | Volume (ml) | Mass Collected (mg) |
|---|---|---|
| 15 | 600 | 361.1 |
| 30 | 300 | 385.0 |
| 45 | 300 | 341.5 |
| 60 | 300 | 361.3 |
| 75 | 275 | 403.2 |
| 90 | 360 | 390.1 |
| 105 | 500 | 557.8 |
| 120 | 600 | 410.5 |
| 136 | 550 | 261.6 |

EXAMPLE 6

Processing of Commercial Proteins and Flours. Hydrolysis by Sequential Enzyme Treatments. Trypsin and Elastase. Soy Flour Soy flour (600 mg) was dispersed in 20 ml 0.01 M potassium phosphate buffer, pH 7.5 with 50 ppm Thimerosal. 2 Mg of trypsin was added and the mixture was placed in 12/14K MWCO dialysis tubing. The mixture was dialysed against 50 ml of buffer at 37° C. in a shaking water bath. The buffer was changed after 2 hours and 6 hours and the dialysis continued for 24 hours. 50 ppm Thimerosal was added to the 6 hour buffer. This procedure was carried out in triplicate.

The 2, 6 and 24 hour permeate samples for each of the triplicate dialysis samples were combined, absorbance at 280 nm determined and the samples evaporated in a 55° C. vacuum oven. The three evaporation residues were reconstituted with 20 ml deionized water, 50 ppm in Thimerosal.

2.0 mg of elastase (0.182 ml of elastase solution, 11 mg protein/ml) was added to each and the samples were placed in 12/14K MWCO dialysis tubing and dialysed against buffer. The buffer was changed after 6 hours and dialysis was continued for 24 hours. After determining absorbance at 280 nm, the permeates were evaporated as described above.

Material so-obtained was designated as sequentially-treated trypsin/elastase soy, MW <12/14K

EXAMPLE 7

Enhancement of Terlakiren Oral Absorption by Protecting Agents in Dogs

Renin antagonist tripeptide terlakiren (200 mg of solid crystalline drug powder in a hard gelatin capsule formulation) was coadministered to four fasted Beagle dogs with an aqueous slurry of 1 g of the test inhibitor in 150 ml water. Serum levels of tripeptide were measured a 6 time points post-dose: 15 min, 30 min, 1 hr, 2 hr, 3 hr and 4 hr. Four fasted dogs were used for each study, each serving as its own control on a preceding week. Serum was extracted with N-butyl chloride followed by incubation with an aqueous solution of chymotrypsin. The degradation product was assayed, after derivitization with fluorescamine. The fluorescence detector was a Kratos Spectroflow 280. The column was a Waters Novapak C-18. The emission wavelength was 380 nm. The mobile phase was 75:25 water:acetonitrile and flow rate 1.0 ml/min. The detection limit was 10 ng/ml. Zero-to-four-hour areas under curves (AUCs) were calculated from the concentration-vs-time plots for each dog using the trapezoidal rule.

Table II demonstrates that commercially available soy protein (PP 620 from Protein Technologies Inc.) and a 1 30K fraction of processed soy flour (prepared as in Example 3) enhance the oral bioavailability of terlakerin, a chymotrypsin-labile therapeutic agent.

TABLE II

Area under the plasma level vs. time curve (AUC) for dogs
AUC ($\mu$g-hr/ml)

| Formulation | Dog # 34112 | 34101 | 04132 | 04094 | Mean |
|---|---|---|---|---|---|
| PP620 | 0.863 | 0.436 | 0.117 | 0.417 | 0.458 |
| Soy (1–30K) | 0.420 | 0.320 | 0.078 | 0.326 | 0.286 |
| Control | 0.043 | 0.026 | 0.022 | 0.106 | 0.049 |
| Ratio: PP620/Control | 20.1 | 16.8 | 5.3 | 3.9 | 11.5 |
| Soy (1–30K)/ Control | 9.8 | 12.3 | 3.5 | 3.1 | 7.2 |

EXAMPLE 8

Protection from Chymotrypsin Degradation of Terlakiren; In Vitro Methodology A standard procedure was employed to assess the in vitro inhibitory potency of various proteins and processed products thereof vs the chymotrypsin degradation of terlakiren, as follows. Test solutions of alpha-chymotrysin ($0.67 \times 10^{-7}$M), terlakiren (0.065 mM) and the test inhibitor (at concentrations of about 0.1 to/or 0.5 mg/ml) were prepared in a pH 6.5 citric acid (0.10 M)/disodium phosphate (0.20M) buffer at a final buffer concentration of 300 mOsm and incubated 37° C. Samples were taken at times 0 and then at 5 minute intervals, quenched with HCl to pH 2.0 preparatory to HPLC analysis. HPLC analysis of terlakiren was carried out using a Waters Resolve 5u C-18 column. The mobile phase was a water:acetonitrile (50:50) mixture to which was added 1 ml of phosphoric acid per liter. Data was expressed as % inhibition of terlakiren degradation based on comparison with time 0 control value, as calculated from the following equation:

$$\% \text{ inhibition} = 100 \times [1 - k_{inh}/k_c]$$

where $K_{inh}$ is the initial degradation rate of terlakiren in the presence of the protecting agents and $k_c$ is the initial degradation rate of terlakiren without protecting agents.

% Inhibitions were determined on decanted, ultrafiltered soy flour, 1K–30K fraction, as shown in Table III.

TABLE III

Reduction of chymotrypsin - catalyzed degradation of terlakiren by the 1–30K fraction of decanted, ultrafiltered Soy flour

| Inhibitor Concentration (mg/ml) | Inhibitor Concentration* (mg protein/ml) | % Inhibition |
| --- | --- | --- |
| 0.5 | 0.04905 | 75.4 |
| 0.25 | 0.02453 | 79.8 |
| 0.1 | 0.00981 | 21.5 |
| 0.05 | 0.00491 | 29.3 |
| 0.01 | 0.00098 | 4.8 |

*Corrected for protein content.

EXAMPLE 9

αa-Chymotrypsin Hydrolysis of Terlakiren Methodology to Determine Ki Values of Inhibitors Ki is defined as the inhibition Michaelis-Menton constant—a conventional measure of the affinity of an inhibitor for the active site and, hence, its potency as an inhibitor of the enzyme. Ki determinations can be carried out from the initial degradation rate data acquired at several concentrations of inhibitor at constant substrate and enzyme concentrations. Initial rates are expressed as millimoles terlakiren degraded per minute, as shown in Table IV.

TABLE IV

Reduction of chymotrypsin-catalyzed degradation of Terlakiren by 1K-30K Decanted and Ultrafiltered Soy Flour

| Inhibitor Concentration (mg/ml) | Inhibitor Concentration** (mg protein/ml) | k* (m mol/min) |
| --- | --- | --- |
| 0.5 | 0.04905 | $1.93 \times 10^{-4}$ |
| 0.25 | 0.02453 | $1.59 \times 10^{-4}$ |
| 0.1 | 0.00981 | $6.17 \times 10^{-4}$ |
| 0.05 | 0.00491 | $5.56 \times 10^{-4}$ |
| 0.01 | 0.00098 | $7.48 \times 10^{-4}$ |
| Pooled control | | $7.86 \times 10^{-4}$ |

*Initial rate loss of Terlakiren
**Corrected for protein content.

Alternatively, determination of Ki for a single inhibitor concentration ("single-point Ki") can be carried out using the standard Michaelis-Menton equation for competitive inhibition. Determination of Ki for multiple concentrations ("multiple-point Ki") can be carried out using the same relationship, fitting the data to the equation using nonlinear regression analysis.

EXAMPLE 10

The dissolution time is an important factor for the performance of the protecting agents of this invention. For the purpose of this disclosure, the reported dissolution time is the time required for a 0.5 mg/ml slurry of the test solid to dissolve completely in a 0.1 M citric acid/0.2M disodium phosphate pH 7 buffer at room temperature rotating end over end at 8 rpm. Visual inspection was used to determine the endpoint for complete dissolution.

EXAMPLE 11

The % protein was determined for various materials which are protecting agents. The concentrations of carbon, hydrogen, and nitrogen in the sample were determined using a Perkin-Elmer 2400 C, H, and N Elemental Analyzer. Approximately two mg of sample was accurately weighed and placed into the analyzer. The % nitrogen in the sample was multiplied by 6.25 to give the estimate of % protein.

EXAMPLE 12

The ability of a variety of commercial and processed protein fractions to reduce the degradation of terlakiren by chymotrypsin was determined. Soy flour was from Sigma Chem. Co.; almond flour and peanut flour were from Pert Labs; wheat gluten was from Total Feeds Corp.

Soy flour from Sigma Chemical Co. is unroasted, and thus contains active Bowman-Birk trypsin/chymotrypsin inhibitor, which has an 8000 MW.

Soy protein (#PP620) from Protein Technologies, Inc. is a heat-treated preparation, in which the Bowman-Birk trypsinichymotrypsin inhibitor has been inactivated. Percent inhibition was determined as described in Example 8. Table V demonstrates that the tested protecting agent fractions reduce the chymotrypsin-catalyzed degradation of terlakiren, a chymotrypsin-sensitive renin inhibitor.

TABLE V

In vitro Inhibition of Degradation of Terlakiren by
Commercial and Processed Proteins (0.5 mg/ml)

| Material Source/Description | % Inhibition (according to Example 8) |
|---|---|
| 1. Soy flour, pepsin-treated and dialysed (>1K) | 87 |
| 2. Soy four, pepsin-treated and fractionated (Example 4) | |
| 1000–3500 MW | 24.0 |
| 3500–6/8K MW | 48.8 |
| 6/8K–12/14K MW | 85.1 |
| 3. Soy Flour | 69.9 |
| 4. Soy flour, decanted and ultrafiltered | |
| 1K–30K MW | 75.4 and 93.3 (two preparations) |
| 30K–100K MW | 75.4 and 88.8 (two preparations) |
| 5. Soy Flour, >1000 MW dialysis | 97.6 |
| 8. Wheat gluten, decanted and ultrafiltered 1K–30K MW | 95.8 |
| 7. Wheat Gluten | 76.8 |
| 8. Peanut flour, decanted and ultrafiltered 1K–30K MW | 28.6 |
| 9. Almond flour, decanted and ultrafiltered 1K–40K MW | 37.6 |
| 10. Soy Protein (Protein Tech., Inc.) | 86.0 |

EXAMPLE 13

For a variety of commercially available protein materials and for processed protein fractions, the % protein, dissolution time, and Ki were determined (as described in Examples 11, 10, and 9, respectively). These data are presented in Table VI. These data demonstrate that degradation-reducing fractions can be prepared which exhibit both a low Ki and a short dissolution time.

Soy flour from Sigma Chemical Co. is unroasted, and thus contains active Bowman-Birk trypsin/chymotrypsin inhibitor, which has an 8000 MW.

TABLE VI

Dissolution Rate and Inhibition Constants of Representative
Commercial and Processed Protein

| Material Source/Description | % Protein | Dissolution Time | Determined Ki |
|---|---|---|---|
| A. Commercial Proteins/Flours | | | |
| 1. Casein (Sigma C-5890) | 87.94 | >4 days | 0.240* |
| 2. Soy Flour | 51.69 | >4 days | 0.18* |
| 3. Wheat Gluten | 78.81 | >4 days | 0.091* |
| B. Ultrafiltered (1K–30K) Substances | | | |
| 1. Soy Flour | 9.81 | 0.1 min | 0.00765 |
| 2. Almond Flour | 10.37 | 2.3 min | 0.0618* |
| 3. Casein | 71.31 | 1.8 min | — |
| 4. Peanut Flour | 13.19 | 3.1 min | 0.120* |
| 5. Wheat Gluten | 37.81 | 3.8 min | 0.0060* |
| C. Ultrafiltered (30K–100K) Substances | | | |
| 1. Soy Flour | 44.44 | 2.6 min | 0.0029 |
| D. Dialysis, >1K | | | |
| 1. Soy Flour | 76.5 | >4 days | 0.010 |
| E. Ultrafiltered, Pepsin-Treated (<30K) | | | |
| 1. Soy Flour (Ex. 16) | 80.1 | 0.1 min | 0.0094 |

*single-point Ki estimation (concentration of inhibitor 0.5 mg/ml)

EXAMPLE 14

Rabbit Intestinal Brush Border Membrane Vesicle (BBMV) Enzymatic Degradation of Cholecystokinin-8 (CCK-8). Inhibition by Soy Protein Fractions.

Rat jejunal brush border membrane vesicles (BBMV) were prepared according to the method of Kessler et al (Biochem. Biophys. Acta 506 (1978) 136). BBMV (25 microgm protein) were incubated with CCK-8 (10 micromolar) in the presence and absence of protecting agents (0.15 mg/ml) in a total volume of 1 ml, at 37° C. Samples were withdrawn at 1 and 3 minutes, were quenched by acetonitrile in an ice bath, and were assayed for undegraded CCK-8 using a high performance liquid chromatography assay. Data presented in Table VII demonstrate that two different molecular weight fractions of processed soy protein were active as inhibitors of the degradation of CCK-8 by BBMV proteases, presumably aminopeptidases.

TABLE VII

Degradation of CCK-8 by BBMV protease. Effect of fractionated soy protein.
% CCK-8 Remaining

| Incubation Time | | 1K–30K MW | 30K–100K MW |
|---|---|---|---|
| (min) | No inhibitor | Inhibitor | Inhibitor |
| 1 min | 42% | 59% | 67% |
| 3 min | 8% | 10% | 16% |

EXAMPLE 15

Protection against degradation by aminopeptidase in vivo.

The pentapeptide enkephalin analogue D-AJa-D-Leu-enkephalin (YdAGFdL) (1.0 mg) was directly ileally dosed to chronically ileally fistulated rats. Radiolabeled YdAGFdL (1.12 microgram) was dosed with each of four protecting agents: (1) decanted soy flour, <1K MW; (2) decanted and ultrafitered soy flour, 1K-30K MW; (3) pepsin-treated (FMC ACTI-MOD) soy flour, <30K MW; (4) the potent aminopeptidase inhibitor amastatin (positive control). Blood was collected from a jugular vein cannula at various times post-dosing, and intact YdAGFdL was quantified by a radiometric thin layer chromatography (TLC) method utilizing reverse phase KC-18 TLC plates (Whatman Co.). The TLC plates were developed with 30:701 -propanol/0.1 M phosphate buffer (pH 4.1).

Table VIII presents absolute bioavailabilies from various treatments. The pepsin-treated (FMC ACTI-MOD) soy flour (MW <30K) was particularly effective as a protecting agent against intestinal aminopeptidases, as evidenced by an almost 11-fold increase in % absorbed. The potent aminopeptidase inhibitor amastatin was also effective, demonstrating that the bioavailability of YdAGFdL is partially limited by degradation by intestinal aminopeptidases. Unroasted soy flour offered no protection to degradation by intestinal aminopeptidases.

TABLE VIII

| Protecting Agent | n | % YdAGFdL Bioavailability |
|---|---|---|
| None (control) | 16 | 1.78 ± 0.46 |
| Decanted soy flour; <1K MW (100 mg) | 4 | 1.74 ± 0.88 |
| Decanted, ultrafiltered soy flour (FMC ACTI-MOD); 1K–30K MW 150 mg) | 4 | 2.76 ± 1.43 |
| Pepsin-treated soy flour; <30K MW (100 mg) | 4 | 19.54 ± 13.75 |
| Amastatin (1 mg) (positive control, Sigma Chemical Co.) | 6 | 8.76 ± 4.47 |
| Say Flour, Unroasted (Sigma) 50 mg | 2 | 1.88 ± 0.67 |

EXAMPLE 16

Preparation of Pepsin-Treated Soy Flour, Using Immobilized Pepsin

Soy flour (Sigma Chem. Co.) (36 gm) was suspended in 1080 ml water and 120 ml of a 0.1% (w/v) solution of Thimerosol. The suspension was mixed at room temperature for 24 hr, and centrifuged for 1 hr at 3600 rpm. The supernatant was ultrafiltered using a 30K MWCO membrane. The >30K MW fraction was collected, concentrated, and adjusted to pH 2 with 0.5 N HCl. This >30K MW fraction was fed into an ACTI-MOD spiral reactor module loaded with 8 gm immobilized pepsin (FMC Corp., Pinebrook, N.J.). The outflow of the enzyme reactor was ultrafiltered using a 30K MWCO membrane. The <30K MW fraction was saved, and the >30K MW fraction was recirculated through the enzyme reactor. After 2 hr total enzyme treatment and ultrafiltration, the total <30K MW fraction was saved, and was designated "Ultrafiltered, Pepsin-Treated (<30K) Soy Flour".

EXAMPLE 17

Inhibition of Trypsin—Catalyzed Degradation of Benzoyl-Arginine-para-Nitroanilide In Vitro The following procedure was employed to assess the in vitro inhibitory potency of a protecting agent of this invention vs the trypsin-catalyzed degradation of benzoyl-arginine-para-nitroanilide (BAPNA). Test solutions of trypsin (1.25 ug/ml, 103 BAEE units/ml), BAPNA 0.5 mg/ml, and test inhibitor (0.5 mg/ml) were prepared in a pH 8 TRIS (0.048 M)/$CaCl_2$ (0.019 M) buffer containing 3.75 ug/ml of bovine serum albumin and incubated at 37° C. Samples were taken at 5 minutes and then at 5 minute intervals up to 40 minutes and quenched with an equal volume of 30% v/v acetic acid preparatory to analysis. Analysis of the decay product of BAPNA hydrolysis, 4-nitroaniline, was carried out using a Perkin-Elmer Lambda 3B UV/Vis Spectrophotometer. Absorbance of the quenched samples was measured at 410 nm. Data were expressed as % inhibition of BAPNA degradation based upon comparison with a control, which contained no inhibitor, as calculated from the following equation:

$$\% \text{ inhibition} = 100\% \times [1-(S_{inh}/S_o)],$$

where, $S_{inh}$ is the rate of change of absorbance with time in the presence of inhibitor and $S_o$ is the rate of change of absorbance with time in the absence of inhibitor.

Percent inhibition was determined using filtered soy flour, 30K–100K fraction. This lot of processed soy flour was prepared according to the solubilization and ultrafiltration method described in Example 3. The results are given in Table IX and demonstrate that the tested processed protein fraction reduced the trypsin-catalyzed degradation of BAPNA.

TABLE IX

| Inhibitor Concentration | Inhibitor Protein Concentration | |
|---|---|---|
| (mg/ml) | (mb protein/ml) | % Inhibition |
| 0.5 | 0.41 | 73 |

EXAMPLE 18

Additional fractionation and enzyme treatment procedures

The procedures for molecular weight fractionation of proteins and peptides described in Examples 1–8 are varied to produce any desired molecular weight fraction by appropriate choice of ultrafiltration membranes or dialysis membranes. Molecular weight fractionation is also effected by gel chromatography.

Enzymatic treatment, as exemplified in Examples 4–7, is carried out with a single proteolytic enzyme, or with various combinations of proteolytic enzymes, acting concurrently or sequentially. A variety of proteolytic enzymes are used, including but not limited to trypsin, chymotrypsin, elastase, carboxypeptidase, aminopeptidase, pepsin, and collagenase.

The fractionation and enzymatic treatments of Examples 1-8 are applied to a wide variety of proteinaceous materials of animal or vegetable origin. Such proteinaceous starting materials include but are not limited to soy flour, soy protein, wheat gluten, almond powder, peanut powder, casein, and fish protein.

EXAMPLE 19

The ability of a protecting agent to dissolve quickly and to begin acting immediately upon being released in vivo is an important factor for the performance of the degration-reducing agents of this invention. For this purpose, the ability of soy flour and of 30K–100K soy flour, decanted and ultrafiltered, to reduce the degradation of Terlakiren in a dynamic environment were compared in vitro. The in vitro methodology of Example 8 was followed except the test solution contained only enzyme and Terlakiren in buffer. Test inhibitor (soy flour or 30K–100K soy flour, decanted and ultrafiltered) was added at a concentration of 0.01 mg/ml without additional mixing, while solution was shaking at speed 5 in a water bath (American Scientific, model # YB531) at 37° C. Sampling was at 19 seconds, 1 minute, then 2 minute intervals until 11 minutes had elapsed, then at 5 minute intervals for a total of 46 minutes. Quenching, HPLC analysis and data analysis were as in Example 8.

| Test Inhibitor 0.01 mg/ml | k* (m mol/min) | % Inhibition |
|---|---|---|
| Soy flour | 2.96 × 10-4 | 27.1 |
| Soy flour decanted & ultrafiltered 30K–100K | 0.86 × 10-4 | 78.8 |

Although the invention has been described with regard to its preferred embodiments, which constitute the best mode presently known to the inventors, it should be understood that various changes and modifications as would be obvious to one having ordinary skill in this art may be made without departing from the scope of the invention which is defined in the claims.

We claim:

1. A pharmaceutical composition consisting essentially of:
    a biologically effective amount of a proteolytically-labile therapeutic agent; and
    a proteinaceous protecting agent selected from the group consisting of a purified natural flour-derived protein, a molecular weight fractionated flour-derived protein, a solvent-extracted flour-derived protein, a partially hydrolyzed flour-derived protein, a partially hydrolyzed wheat gluten, and a molecular weight fractionated wheat gluten.

2. A pharmaceutical composition according to claim 1, wherein said proteinaceous protecting agent has a molecular weight ranging from approximately 1,000 and approximately 100,000.

3. A pharmaceutical composition according to claim 2, wherein said proteinaceous protecting agent has a molecular weight between approximately 1,000 and approximately 30,000.

4. A pharmaceutical composition according to claim 1, wherein said proteinaceous protecting agent is a partially hydrolyzed protein which has been enzymatically hydrolyzed.

5. A pharmaceutical composition according to claim 4, wherein said partially hydrolyzed protein is enzymatically hydrolyzed with an enzyme selected from the group consisting of trypsin, chymotrypsin, elastase, carboxypeptidase, aminopeptidase, pepsin, and collagenase.

6. The pharmaceutical composition according to claim 1, wherein said protecting agent is derived from the group consisting of soy flour, soy protein, wheat gluten, almond flour, and peanut flour.

7. The pharmaceutical composition according to claim 1, wherein said proteolytically-labile therapeutic agent is calcitonin, prolactin, adenocorticotropin, thyrotropin, growth hormone, gonadotric hormone, oxytocin, vasopressin, gastrin, tetragastrin, pentagastrin, glucagon, secretin, pancreozymin, substance P, gonadotropin, immunoglobulin, leuprolide, luteinizing hormone releasing hormone, enkephalin, cholecystokinin, follicle stimulating hormone, interferon, interleukin, thymopentin, endothelin, neurotensin, insulin, insulintropin, or terlakiren.

8. A pharmaceutical composition according to claim 1, wherein said proteinaceous protecting group is selected from the group consisting of an enzymatically cleaved soy flour fraction having a molecular weight ranging from 6,000 to 14,000, a filtered soy flour fraction having a molecular weight between 1,000 and 100,000, and a dialyzed soy flour fraction having a molecular weight greater than 1,000.

9. A therapeutic administrant comprising the pharmaceutical composition of claim 1, and a pharmaceutically acceptable carrier.

10. A method for administering a proteolytically-labile therapeutic agent, said method comprising the steps of:
    administering to a mammal in need of a therapeutic agent a pharmaceutical composition consisting essentially of a proteolytically-labile therapeutic agent in combination with a protecting agent selected from the group consisting of a purified natural flour-derived protein, a molecular weight fractionated flour-derived protein, a solvent-extracted flour-derived protein, a partially hydrolyzed flour-derived protein, a partially hydrolyzed wheat gluten, and a molecular weight fractionated wheat gluten.

11. A method according to claim 10, wherein said proteinaceous protecting agent has a molecular weight ranging from approximately 1,000 and approximately 100,000.

12. A method according to claim 11, wherein said proteinaceous protecting agent has a molecular weight between approximately 1,000 and approximately 30,000.

13. A method according to claim 10, wherein said proteinaceous protecting agent is a partially hydrolyzed protein which has been enzymatically hydrolyzed.

14. A method according to claim 13, wherein said partially hydrolyzed protein is enzymatically hydrolyzed with an enzyme selected from the group consisting of trypsin, chymotrypsin, elastase, carboxypeptidase, aminopeptidase, pepsin, and collagenase.

15. A method according to according to claim 10, wherein said protecting agent is derived from the group consisting of soy flour, soy protein, wheat gluten, almond flour, and peanut flour.

16. A method according to according to claim 10, wherein said proteolytically-labile therapeutic agent is calcitonin, prolactin, adenocorticotropin, thyrotropin, growth hormone, gonadotric hormone, oxytocin, vasopressin, gastrin, tetragastrin, pentagastrin, glucagon, secretin, pancreozymin, substance P, gonadotropin, immunoglobulin, leuprolide, luteinizing hormone releasing hormone, enkephalin, cholecystokinin, follicle stimulating hormone, interferon, interleukin, thymopentin, endothelin, neurotensin, insulin, insulintropin, or terlakiren.

17. A method according to claim 10, wherein said proteinaceous protecting group is selected from the group consisting of an enzymatically cleaved soy flour fraction having a molecular weight ranging from 6,000 to 14,000, a filtered soy flour fraction having a molecular weight between 1,000 and 100,000, and a dialyzed soy flour fraction having a molecular weight greater than 1,000.

* * * * *